United States Patent [19]

Serbinenko et al.

[11] 4,282,875
[45] Aug. 11, 1981

[54] OCCLUSIVE DEVICE

[76] Inventors: Fedor A. Serbinenko, Kutuzovsky prospekt, 33, kv. 43; Sergei I. Kljuchnikov, Volgogradsky prospekt, 164, korpus 2, kv. 111, both of Moscow, U.S.S.R.

[21] Appl. No.: 6,037

[22] Filed: Jan. 24, 1979

[51] Int. Cl.³ ............................................. A61M 25/00
[52] U.S. Cl. .................. 128/325; 128/349 B; 128/344
[58] Field of Search ............. 128/325, 344, 348–351; 46/87–90

[56] References Cited

U.S. PATENT DOCUMENTS

| 3,834,394 | 9/1974 | Hunter et al. | 128/325 |
| 3,885,561 | 5/1975 | Cami | 128/214 R |
| 4,085,757 | 4/1978 | Pevsner | 128/325 |

*Primary Examiner*—Dalton L. Truluck
*Attorney, Agent, or Firm*—Lackenbach, Lilling & Siegel

[57] ABSTRACT

The proposed device for the occlusion of brain vessels comprises an occlusive bulb of an elastic material. Its thicker head portion accommodates a metal plug, while the tail portion contains a valve made of the material of the bulb itself, through which the tip of a catheter is introduced. The pear-shaped valve points inside the bulb, and its neck bears a spring element.

When the bulb is drawn along an occluded vessel, with better maneuverability, the bulb's cavity is more reliably sealed after the catheter has been detached therefrom.

9 Claims, 7 Drawing Figures

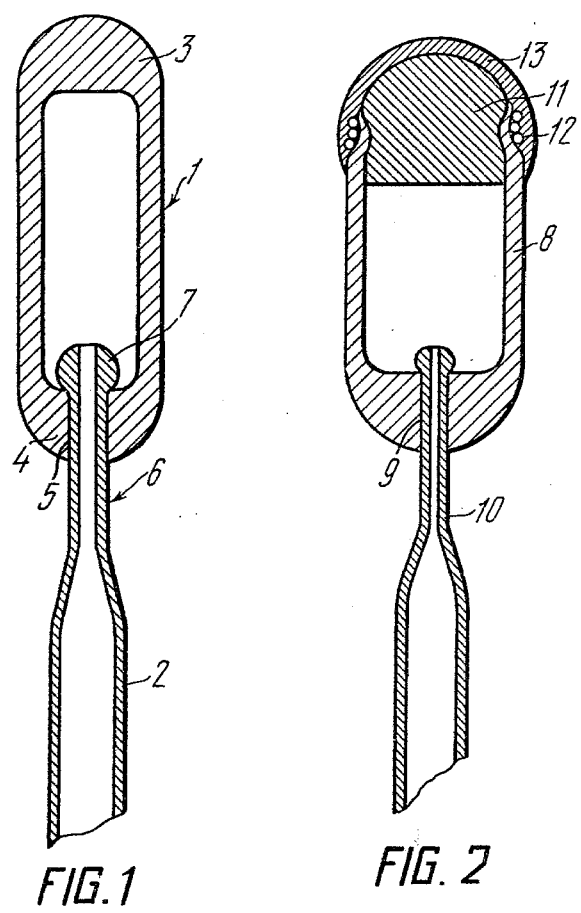

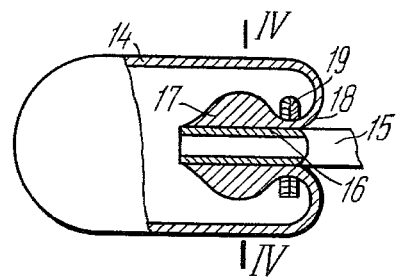
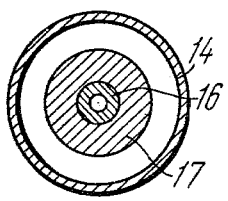
FIG. 3    FIG. 4
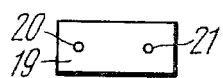
FIG. 5
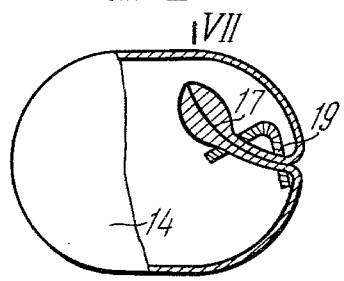
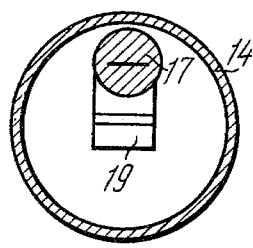
FIG. 6    FIG. 7

OCCLUSIVE DEVICE

BACKGROUND OF THE INVENTION

This invention relates to the field of medicine, particularly to vascular surgery and neurosurgery. More specifically, this invention is intended for the occlusion (plugging) of the lumen of pathological vessels of the brain.

As is known, about 50 percent of arteriovenous aneurysms of the brain are inoperable. Part of them are subjected to the embolization of the afferent vessels feeding the aneurysm.

Contrast plastic or porcelain globules have been used of late for the purpose of embolization of the afferent vessels of cerebral aneurysms. Luessenhop, Spence and Washington (JAMA, 1960, 172, 11, 1153–1155). Kosary et al. (J. Neurosurgery, 1968, 28, 6, 605–608; Neurochirurg. 1971, 14, 3, 98–101).

However, the use of contrast globules is not devoid of disadvantages, among which one may note the necessity of opening the carotid artery for introducing the globules into its lumen; the placement of a vascular suture onto the carotid artery and sometimes its ligation; difficulty in selecting the globules for occluding the cerebral vessels; a globule with a diameter smaller than the vessel to be occluded may penetrate into the distal portions of the vessel, while a globule of a greater diameter may plug the vessel's more proximal portions.

A globule introduced into the lumen of the carotid artery is uncontrollable, and may inadvertently not plug the cerebral vessel intended for occlusion, but another, functionally more important, thereby causing serious cerebral complications, and in some cases causing lethal results.

Known in the art are devices for occluding (plugging) a blood vessel for a curative or diagnostic purpose (cf. U.S. Pat. No. 3,834,394; Cl. 128–325, accepted patent specification in Great Britain Pat. No. 1,333,096, 1973; Cl. A5R). We have taken as the prototype the occlusive device (bulb) according to U.S. Pat. No. 3,834,394.

The prior art device appears as a hollow elastic bulb, its distal and proximal ends being thicker and more elastic than the walls of its body. The proximal end of the bulb contains a canal for temporarily connecting the bulb's cavity with the bore of an internal catheter. The internal catheter lies within the bore of an external catheter. With the aid of this system of catheters the occlusive bulb is carried through a puncture in the wall of a trunk vessel to the required portion of the vessel to be occluded. The internal part of the canal of the bulb's proximal end has a one-way valve (normally closed), comprising a shutter whose plane is situated on the internal opening of the canal perpendicular to its longitudinal axis.

Fillers are introduced into the cavity of the occlusive bulb through the bore of the internal catheter for increasing the volume of the bulb to the size necessary for occluding the vessel. When necessary, contrast agents are introduced into the space formed by the external surface of the internal catheter and the internal surface of the external catheter. At the moment of detachment of the internal catheter from the occlusive bulb, the distal end of the external catheter is thrust against the proximal end of the bulb, thereby ensuring the fixation of the occlusive bulb at the site of the occlusion.

The design of the valve of the device known in the art precludes the withdrawal, when necessary of the filler from the bulb's cavity. It is therefore impossible to diminish the volume of the bulb. Nor does this permit changing a mistakenly chosen site of the occlusion, or the removal from the vessel of a bulb already dilated by the filler in case the patient reveals intolerence to the occlusion.

Besides, during the separation of the catheter from the bulb, inversion of the valve may occur, disrupting the reliable sealing of the bulb's cavity. As a result, the filler will escape from the bulb's cavity, causing spontaneous diminution of its volume and the bulb's travel with the blood flow with subsequent uncontrollable occlusion of vital vessels.

It is an object of the invention to provide an occlusive device which allows reliable plugging of small (0.5 to 0.25 mm) vessels of the brain.

Another object of the invention is to provide an occlusive device that can be drawn along convoluted and branching vessels of the brain.

Still another object of the invention is to provide an occlusive device that may be expanded by fillers to a volume 10–50 times greater than the initial volume of the bulb.

A further object of the invention is to provide an occlusive device whose valve reliably shuts off the bulb's cavity at its maximum volume and will not become inverted during the removal of the catheter from the bulb.

A further object of the invention is to provide an occlusive device capable of being expanded by any liquid fillers to which the patients organism is compatible.

Still another object of the invention is to provide an occlusive device whose connection with the catheter is sufficiently strong to preclude the bulb from being detached from the catheter by the blood flow.

The final object of this invention is to provide an occlusive device which dampens its own vibration due to the turbulent flow of the blood when the bulb is advanced towards the vessel to be occluded.

SUMMARY OF THE INVENTION

The present invention resides in an occlusive device predominantly for plugging the vessels of the brain, comprising a thin-walled bulb made of an elastic material having a thicker part in its head and tail portions, with an elastic catheter being introduced into its self-closing aperture for feeding a filling agent into the bulb therethrough.

This device is characterized by the thicker head part of the bulb comprising a metal plug while the thicker tail part comprises a valve made of the same material as the bulb, shutting off the bulb's aperture when the distal tip of the catheter, having a clamp, is removed, said tip being of a relatively smaller diameter and greater elasticity than the catheter's main body.

According to an embodiment of this invention, an occlusive device is proposed, wherein said valve is made in the form of a pear-shaped body pointing towards the internal cavity of the bulb with a self-closing slit-like canal for the introduction of a catheter, with a compressed spring element set on the neck of said pear-shaped valve, said element straightening upon the removal of the catheter and bending the neck of the pear-shaped valve.

According to still another embodiment of the invention, an occlusive device is proposed, wherein said relatively thinner tip of the catheter introduced into the bulb is provided with a spherical clamping head.

These technical solutions permit dampening the vibration of the bulb, caused by the turbulent blood flow, when said bulb advances towards the vessel to be occluded; increase the reliability of the bulb's closure and preclude the escape of dilating substances from its cavity following the removal of the catheter; ensure the mobility of the advancing bulb along the convoluted and branching vessels of the brain; increase the reliability of the bulb to catheter connection and preclude detachment of the bulb from the catheter by the blood flow in the vessel.

BRIEF DESCRIPTION OF THE DRAWINGS

The invention will now be described in greater detail with reference to preferred embodiments thereof, taken in conjunction with the accompanying drawings, wherein:

FIG. 1 shows an occlusive device according to the invention in its simplest embodiment;

FIG. 2 is the device of FIG. 1 with a metal plug in the bulb;

FIG. 3 represents an embodiment of the bulb of the occlusive device with a pear-shaped valve;

FIG. 4 is a section view taken along line IV—IV of FIG. 3;

FIG. 5 shows the spring element in the device of FIG. 3;

FIG. 6 shows the bulb of the device of FIG. 3, following the removal of the catheter;

FIG. 7 is the device of FIG. 6 (section along VII—VII).

DETAILED DESCRIPTION OF THE INVENTION

The occlusive device (FIG. 1) comprises two basic parts: a hollow bulb 1, made of latex, and a polyethylene catheter 2, connected to said bulb. The dimensions of the bulb and the length of the catheter may vary depending on the diameter of the vessel to be occluded and its distance from the puncture site on the carotid artery. The head portion 3 of the bulb 1 is opaque to X-rays which allows conducting X-ray-TV monitoring when introducing the bulb 1 into a vessel. The thicker tail portion 4 is the sphincter of the bulb 1 and has an aperture 5 which fulfils the function of an elastic connection between the bulb 1 and catheter 2. By virtue of the connection between the surface of the aperture 5 with the thinner part 6 of the catheter 2, the bulb 1 is firmly held on the catheter during the passage through the blood flow. The bulb 1 is firmly secured on the catheter 2 by the clamping bulge 7 on its tip which is in the bulb's cavity.

Upon the detachment of the bulb from the catheter and the removal of the latter from the carotid artery, the thicker tail part of the bulb 4 fulfils the role of a sphincter precluding the escape of expanding substances from the bulb's cavity. The spherical shape of the head 3 and tail 4 portions of the bulb facilitate both the passage of the bulb along the vessel, and its removal thereof, if the operation for some reason cannot be performed. The thinner portion 6 of the catheter 2 ensures the mobility of the bulb in the vessel and makes it possible to retain it in the center of the blood flow.

An example will now be described of using the device for the artificial stationary occlusion of blood vessels.

For excluding the afferent vessels of an arteriovenous aneurysm of the brain under local anesthesia, the patient's carotid artery is punctured in the neck with a hollow needle having a 1.3–1.5 mm bore. A polyethylene catheter with an elastic latex bulb secured on its end, is introduced into the artery through the needle. The bulb is advanced by the surgeon by means of the catheter and under X-ray-TV monitoring into the proper portion of the brain. After bringing the bulb to the vessel to be occluded a contrast medium (0.1–0.2 $cm^3$) is introduced through the catheter into the bulb's cavity whereby the bulb is extended to the dimensions necessary from the complete occlusion of the vessel. The temporary occlusion of the vessel is maintained for 10–15 minutes for determining the possibility of the stationary exclusion of the vessel under examination. If the patient can tolerate the temporary occlusion for 10–15 minutes, a stationary occlusion of the vessel is performed by introducing a filler (physiological solution, glucose solution, contrast medium, fast-setting plastic, etc.) into the bulb. Then, by slightly pulling outward, the surgeon detaches the catheter from the bulb and withdraws the catheter from the lumen of the vessels. The hollow puncture needle is also removed from the carotid artery. Upon the detachment of the catheter the sphincter in the rear part of the bulb contracts and shuts off the aperture which temporarily held the catheter. Thus, the spincter prevents the escape of the filler from the bulb. The bulb remains in the lumen of the vessel, completely occluding its lumen.

In accordance with another embodiment, an occlusive bulb 8 (FIG. 2) has in its proximal end a self-closing aperture 9, temporarily comprising the working part of a catheter 10. The bulb 8 is shaped as a sleeve and a plug 11 secured by a ligature 12, is arranged in its open distal part.

For streamlining the nonuniformity of the distal end of the bulb, the protruding part of plug 11 and ligature 12 are covered by a protective latex cap 13.

An example of the functioning of the device will now be described.

Under local anesthesia and following the puncture of the carotid artery in the neck with a hollow needle, the catheter 10 with the bulb 8 temporarily secured on it are introduced through the needle's bore. After the bulb 8 is advanced under X-ray-TV monitoring to the site of the intended occlusion, a contrast medium is introduced into the cavity of the bulb 8 through the catheter 10 which expands the bulb until the complete occlusion of the pathological vessel. When the surgeon is satisfied that the patient can tolerate the temporary occlusion, the contrast medium is removed from the bulb and its cavity is expanded with a fast-setting plastic. After the plastic sets, the surgeon pulls the catheter 10 slightly, to detach it from the bulb 8. The catheter and the hollow needle are removed from the carotid artery while the expanded bulb remains in the pathological vessel, occluding its lumen.

The arrangement of the metal plug 11 in the distal end of the bulb 8 makes the latter heavier and the bulb is less affected by the turbulent blood flow and its vibration in the vessel is dampened. Besides, the metal plug 11, being opaque to X-rays, serves as a marker facilitating X-ray-TV monitoring when advancing the bulb to the required blood vessel.

Another improved embodiment of the invention will now be described.

FIGS. 3 and 4 show an occlusive bulb 14 with a catheter 15, temporarily placed in the slit-like canal 16, passing within the pear-shaped body of the valve 17 and the neck 18 of the valve 17. Situated on the neck 18 is a horseshoeshaped spring element 19.

An example of the operation of the occlusive bulb 14 with the pear-shaped valve 17 in this embodiment will now be described when used for occluding pathological cerebral vessels (the operation is performed under local anesthesia and X-ray-TV monitoring).

The occlusive bulb 14 with catheter 15 temporarily connected thereto is introduced into the cavity of the carotid artery through the bore of a needle following the puncture of the wall of the external carotid artery with said hollow needle. The distal end of the catheter 15 is introduced into the slit-like canal 16 of the valve 17, which, expanding tightly embraces the catheter 15, which provides for communication of the bore of the catheter 15 with the cavity of the bulb 14 for expanding the latter by a filler. Situated behind the body of the valve 17, on its neck 18, is the bent spring element 19, which compresses the neck 18 of the valve 17 with its self-closing apertures 20 and 21, thereby ensuring a sealing contact between the walls of the slit-like canal 16 with the external surface of the distal tip of the catheter 15. The occluding bulb 14 is advanced by means of the catheter 15 into the cerebral vessel, to be occluded, and through the bore of the catheter a filler (contrast medium) is introduced into the bulb's cavity. After the bulb is expanded by the filler to dimensions necessary for the complete occlusion of the vessel, the surgeon pulls the catheter slightly to detach it from the bulb secured in the lumen of the vessel.

During the removal of the catheter from the filler expanded bulb, forces tending to invert the valve outside the bulb appear, due to the catheter clinging to the walls of the slit-like canal.

However, no inversion of the valve takes place, since the body of the valve 17, thicker than the neck 18, being drawn outside by the catheter 15, is thrust against the spring element 19, which in turn is thrust against the internal wall of the proximal end of the bulb.

As the catheter 15 leaves the bulb 14, the walls of the slit-like canal 16 begin to close up due to the elastic properties of the valve's material. Upon the removal of the catheter from the bulb, the tight closure of the walls of the slit-like canal 16 is ensured on account of the compression of the neck 18 by the self-closing apertures 20 and 21 of the spring element 19.

Additional sealing of the valve is affected also by the bending of the neck of valve 17 by the spring element 19 which tends to straighten out.

The detached catheter is removed from the vascular bed and the bulb expanded by the filler remains in the pathological vessel, occluding its lumen.

Compared to the prior art devices, the occlusive bulb of the proposed design for plugging blood vessels provides the following advantages.

The possibility of repeated introduction and withdrawal of the filler from the bulb cavity, which allows selecting the site of occlusion with greater precision, and in cases of intolerance to the occlusion by the patient, rapid removal of the bulb from the vascular bed.

Inversion of the valve is precluded, thereby increasing reliability of the closure of the bulb's cavity in the process of detaching the catheter from the bulb and thereafter.

The possibility of a decrease in the volume of the bulb through escape of the filler with subsequent dangerous uncontrollable occlusion of vital vessels, is reduced.

The highly reliable shut-off of the bulb's valve permits the use of any liquids to which the human organism is compatible, as fillers.

What is claimed is:

1. An occlusive device for use in plugging blood vessels of the brain, comprising:
    an elastic catheter having a distal tip with an opening therethrough, said distal tip having a thin walled elastic bulb releasably mounted thereon, said bulb having a thick spherical head portion accommodating a metal plug which provides means to dampen vibrations caused by the flow of blood, and a thick spherical tail portion containing a self-closing aperture surrounding and housing said distal tip of said catheter, wherein said aperture functions as a valve which closes upon removal of the distal tip of said catheter from the elastic bulb; said distal tip of the catheter having connecting or coupling enlargement means thereon which extends through the tail portion and which internally secures the tip within the bulb cavity said enlargement means adapted to prevent detachment of the tip from the bulb by the flow of blood; and wherein the opening in the distal tip of the catheter is relatively smaller in diameter and has a greater elasticity than the main body of the catheter.

2. An occlusive device as claimed in claim 1, wherein the aperture-valve has a pear-shaped body with a central, longitudinal, self-closing canal directed towards the bulb cavity, which accommodates the introduction of the catheter, and clamping means on the neck of the pear-shaped valve, which, upon removal of the catheter, compress the neck and close the pear-shaped valve.

3. An occlusive device as claimed in claim 1, wherein the end of the distal tip of the catheter, is spherical in shape.

4. An occlusive device as claimed in claim 1, wherein the bulb is made of latex, and the catheter is made of polyethylene.

5. An occlusive device as claimed in claim 1, wherein the metal plug is x-ray detectable.

6. An occlusive device as claimed in claim 1, wherein said clamping means consist of a compressed spring element.

7. An occlusive device as claimed in claim 1, wherein said bulb contains a filler medium compatible to the human organism.

8. An occlusive device as claimed in claim 1, wherein the aperture-valve is a sphincter.

9. An occlusive device for use in plugging blood vessels of the brain, comprising:
    an elastic catheter having a distal tip with an opening therethrough, said distal tip having a thin walled elastic bulb releasably mounted thereon, said bulb having a thick spherical head portion accommodating a metal plug which provides means to dampen vibrations caused by the flow of blood, and a thick spherical tail portion containing a self-closing aperture surrounding and housing said distal tip of said catheter, wherein said aperture functions as a valve which closes upon removal of the distal tip of said catheter from the elastic bulb; said valve aperture having a pear-shaped body with a central, longitudinally self-closing canal directed towards the bulb cavity, which accommodates the introduction of the catheter, and connecting or coupling means on the neck of the pear-shaped valve, which upon removal of the catheter, compress the neck and close said pear-shaped valve; the distal tip of said catheter thereby being prevented from detaching from the bulb by the flow of blood; and wherein the opening in the distal tip of the catheter is relatively smaller in diameter and has a greater elasticity than the main body of the catheter.

* * * * *